(12) United States Patent
Majeed et al.

(10) Patent No.: US 7,063,861 B2
(45) Date of Patent: Jun. 20, 2006

(54) BIOAVAILABLE COMPOSITION OF NATURAL AND SYNTHETIC HCA

(75) Inventors: Muhammed Majeed, Piscataway, NJ (US); Vladimir Hadmaev, Piscataway, NJ (US)

(73) Assignee: Sabinsa Corporation, Piscataway, NJ (US)

( * ) Notice: Subject to any disclaimer, the term of this patent is extended or adjusted under 35 U.S.C. 154(b) by 395 days.

(21) Appl. No.: 09/926,746

(22) PCT Filed: Aug. 17, 2001

(86) PCT No.: PCT/US01/41748

§ 371 (c)(1),
(2), (4) Date: Jun. 6, 2002

(87) PCT Pub. No.: WO02/14477

PCT Pub. Date: Feb. 21, 2002

(65) Prior Publication Data

US 2002/0187943 A1     Dec. 12, 2002

Related U.S. Application Data

(60) Provisional application No. 60/225,821, filed on Aug. 17, 2000.

(51) Int. Cl.
*A61K 9/14* (2006.01)
*A61K 9/20* (2006.01)

(52) U.S. Cl. ............... 424/451; 424/400; 424/439; 424/464

(58) Field of Classification Search ........... 424/400, 424/451, 464, 439
See application file for complete search history.

(56) References Cited

U.S. PATENT DOCUMENTS 6,413,545 B1 *  7/2002  Alviar et al. ............... 424/451

FOREIGN PATENT DOCUMENTS

| EP | 0 787 489 A2 | 8/1997 |
| EP | 0 815 857 A1 | 1/1998 |
| WO | WO 00/12080 | 3/2000 |
| WO | WO 00/54610 | 9/2000 |

OTHER PUBLICATIONS

S. B. Heymsfield, et al., "*Garcinia cambogia* (Hydroxycitric Acid) as a Potential Antiobesity Agent", JAMA: The Journal of the American Medical Association; Nov. 11, 1998, vol. 280, No. 18; pp. 1596-1600.
Patent Abstracts of Japan, Publication No. 10265397, Publication Date: Jun. 10, 1998; Title: Agent for Preventing Obesity; Applicant: Oruto Corp:KK.

* cited by examiner

*Primary Examiner*—Carlos A. Azpuru
(74) *Attorney, Agent, or Firm*—Arent Fox PLLC

(57) ABSTRACT

The invention relates to a composition comprising hydroxycitric acid (HCA) in combination with either one or both of garcinol and anthocyanin, and its use as a weight-loss therapy in animal subjects, preferably humans. The therapeutic effects for the composition observed in murine and human studies include a reduction in total body weight and body mass index, a reduction in body fat, an increase in lean body mass and content of body water, and a reduction in perceived appetite level. Another composition for use in weight-loss therapy is also described relating to forskolin in combination with either one or both of garcinol and anthocyanin. The anti-oxidant properties of garcinol are described as being enhanced in the presence of HCA and anthocyanin, and the combination of HCA, garcinol and anthocyanin is also shown to exert greater citrate lyase inhibiting properties than either compound alone. Methods of obtaining HCA, garcinol or anthocyanin, or a composition containing all three compounds, are described.

17 Claims, 19 Drawing Sheets

BIOAVAILABLE COMPOSITION OF NATURAL AND SYNTHETIC HCA

CROSS-REFERENCE TO RELATED APPLICATION

This application is a National Stage entry of International Application No. PCT/US01/41748, filed on Aug. 17, 2001, which claims priority under 35 USC §1.119(e) to provisional Application Ser. No. 60/225,821, filed on Aug. 17, 2000, the entire specification, claims and drawings of which are incorporated herewith by reference.

BACKGROUND OF THE INVENTION

Hydroxycitric acid is an alpha-hydroxy tribasic acid (1,2-dihydroxypropane-1,2,3-tricarboxylic acid) with two asymmetric centers, hence the formation of two pairs of diasteroisomers or four different isomers: (−)hydroxycitric acid (I), (+)hydroxycitric acid (II), (−)allo-hydroxycitric acid (III), and (+)allo-hydroxycitric acid (IV). (1–2) The (−)hydroxycitric acid (HCA) isomer is found in the rind of Garcinia cambogia fruit (fam. Clusiaceae). (1–2) This isomer has been shown to be a potent linear competitive inhibitor of ATP citrate lyase enzyme, in vitro, demonstrating a much greater affinity for the purified enzyme than its natural substrate citrate as well as the other stereoisomers of hydroxycitric acid. (1–2) The biological importance of ATP citrate lyase is as a citrate cleavage enzyme which catalyzes the extramitochondrial cleavage of citrate to acetyl CoA and oxaloacetate, and facilitates the biosynthesis of fatty acids. The reversible inhibition of citrate lyase by (−) HCA may lead to the reduction of fatty acids synthesis and lipogenesis. These effects have been measured and demonstrated in vivo following the oral, intravenous or intraperitoneal administration of (−)hydroxycitrate to experimental animals. (3) When (−) HCA was given orally before the feeding period, the animals fed (−) HCA consumed less food and their hepatic synthesis of fatty acids and cholesterol was significantly diminished as compared to the untreated controls. (3–4) The observed decrease in food intake may be only one of the factors responsible for the (−) HCA promoted weight loss, because experimentation with rats fed (−) HCA showed weight loss with no decrease in cumulative food intake. (5) It seems that the potential mechanism of weight loss with (−) HCA may include an energy expenditure component, the nature of which remains undetermined. (5) This mechanism of energy expenditure, decreased lipogenesis, and the reduction in food intake in (−) HCA-treated animals may result in loss of weight and total body fat content. (6)

Although the potential of (−)HCA as a weight lowering compound has been recognized since the 1970's, only few clinical studies have been conducted with this compound. (7–12). These few studies examining HCA-mediated prevention of excess body fat, resulted in contradictory results, most likely due to HCA being poorly bioavailable in the cytosol of a target cell. In one clinical study of HCA, a controversial high fiber diet was used. The use of a high-fiber diet in combination with HCA may reduce gastrointestinal absorption of HCA, since high-fiber diets are known to reduce absorption of many nutrients and micronutrients. This issue becomes critical with HCA because its reported efficacy in inhibiting the intracellular enzyme, adenosine triphosphate (ATP)-citrate-lyase, depends entirely on the presence of HCA inside the target cell.

In their U.S. Patent, the Inventors addressed an important issue regarding the bioavailability of the HCA compounds. The U.S. Pat. No. 5,783,603 patent described a manufacturing process leading to a unique structure for a potassium salt of HCA, which facilitated its transport across biological membranes, effectively delivering more HCA into the cytosol for the competitive inhibition of ATP citrate lyase. Although the '603 patent related to an HCA compound having considerably improved bioavailability, its bioavailability was still relatively inefficient. For example, an in vitro study done on hepatic cells, indicates that 5 mM of extracellular potassium HCA could inhibit ATP citrate lyase. However, only 0.5 mM of potassium HCA is actually needed in the cytosol to effectively inhibit ATP citrate lyase. Therefore, a 10-fold excess amount of potassium HCA is needed outside of the target cell in order to achieve a concentration of 1/10 that amount in the cytosol. This finding of relatively poor bioavailability of HCA, was confirmed in pre-clinical experiments (14), and points out the need to further improve the bioavailability and efficacy of HCA.

Garcinol, like HCA, is isolated from Garcinia sp. fruit rind, and it exhibits anti-oxidant and chemoprotective properties (15). In one experiment, rats fed a garcinol diet (0.01% and 0.05%) showed a significantly reduced development of azoxymethane (AOM)-induced colonic aberrant crypt foci (ACF) as compared to control animals. Feeding of garcinol significantly elevated liver glutathione S-transferase, quinone reductase activities, suppressed O2- and NO generation and expression of iNOS and COX-2 proteins. These findings suggest a possible chemopreventive mechanism of garcinol.

Garcinol and isogarcinol were evaluated for their antibacterial activity against methicillin-resistant Staphylococcus aureus (16). These compounds showed a minimum inhibitory concentration at 3.1–12.5 micrograms/ml, or nearly equal to that of the antibiotic, vancomycine.

In 1981, Krishnamurthy et al. (17) reported the isolation of garcinol, and its colorless isomer, isogarcinol, from Garcinia indica. Their structures were proposed on the basis of chemical and spectral data. Garcinol, C38H50O6, m.p. 122(o), crystallized out from the hexane extract of the fruit rind of G. indica as yellow needles (1.5 percent). The UV spectrum of garcinol suggested that the 1,3-diketone system is conjugated to the 3,4-dihydroxybenzoyl moiety. The IR spectrum of the trimethyl ether showed the presence of a saturated carbonyl group (1727 cm−1) and two oe,beta-unsaturated carbonyl groups (1668 and 1642 cm−1).

Isogarcinol was isolated by column chromatography of the extract. Its identity was established by mixed m.p. and by comparison of LN, IR, and PMR spectra. The IR spectrum of isogarcinol indicated the presence of saturated carbonyl group (1715 cm−1), an aroyl group (1670 cm−1) and an oe,beta-unsaturated carbonyl group (1635 cm−1).

Rao et al. (18) reported the isolation of cambogin (33H55O6), m.p. 242–244, from the latex of Garcinia cambogia tree. The structure was confirmed by UV, IR and NMR studies. UV: 231–234, 275–278 and 305–313; IR (Kbr): 1720 (saturated carbonyl), 1680 and 1642 cm−1 (unsaturated carbonyl and double bond). Besides cambogin they also reported the isolation of camboginol and related its structure to cambogin.

In 1982, N. Krishnamurthy et al. (19) isolated anthocyanin pigments from the fresh red ripe fruits of Kokam (Garcinia indica). The rind portion was separated from the rest of the fruit and was macerated in a blender using methanol containing one percent HCl for three times. The extracts were combined, filtered and concentrated in vacuo at 30° C. Paper chromatography of the Kokam pigment extract showed two anthocyanin bands. The slower moving band was designated as B1 and the other B2. The total anthocyanin concentration was estimated to be 2.4 percent on a dry weight basis; the ratio of B1 to B2 is 1:4.

Anthocyanin B1 was identified as cyanidine-three-glucoside by chemical and spectroscopic studies. This compound on hydrolysis gave cyaniding and glucose. The UV spectral maximum (527 nm) of the glycosides shifted to 567 nm with aluminium chloride indicating that 3'- and 4'-hydroxyl groups of the cyaniding are free. The structure was confirmed by direct comparison with a sample of cyaniding-three-glucoside obtained from mulberry.

Anthocyanin B2 was identified as cyaniding-three-sambubioside. This anthocyanin on complete hydrolysis gave cyaniding, glucose and xylose. The spectral data suggested that B2 is a three-substituted glycoside of cyaniding. Hydrogen peroxide hydrolysis removed the disaccharide from the pigment which on further acid hydrolysis gave glucose and xylose. The structure was confirmed by direct comparison with a sample of cyaniding-3-sambubioside isolated from Roselle.

The present invention is based on the unexpected finding that combining HCA with natural compounds obtained from *Garcinia* sp. plant including garcinol (polyisoprenylated benzophenone) and/or anthocyanin compounds, results in not only an enhancement of the biological activity of HCA but also that of garcinol and/or anthocyanin.

DETAILED DESCRIPTION OF THE INVENTION

Figure 1:
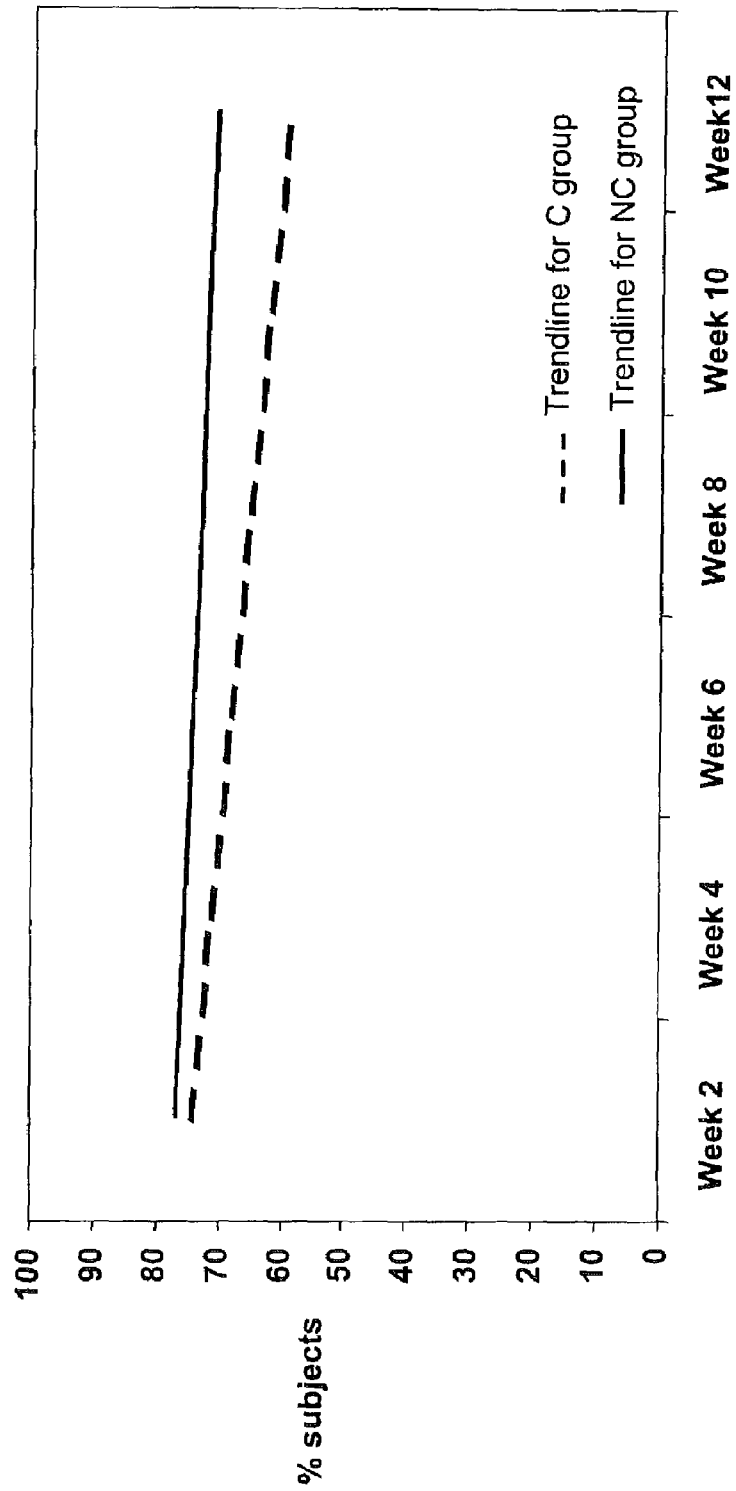
FIG. 1: Trendlines of the percentage of subjects who experienced weight loss.
Figure 2:
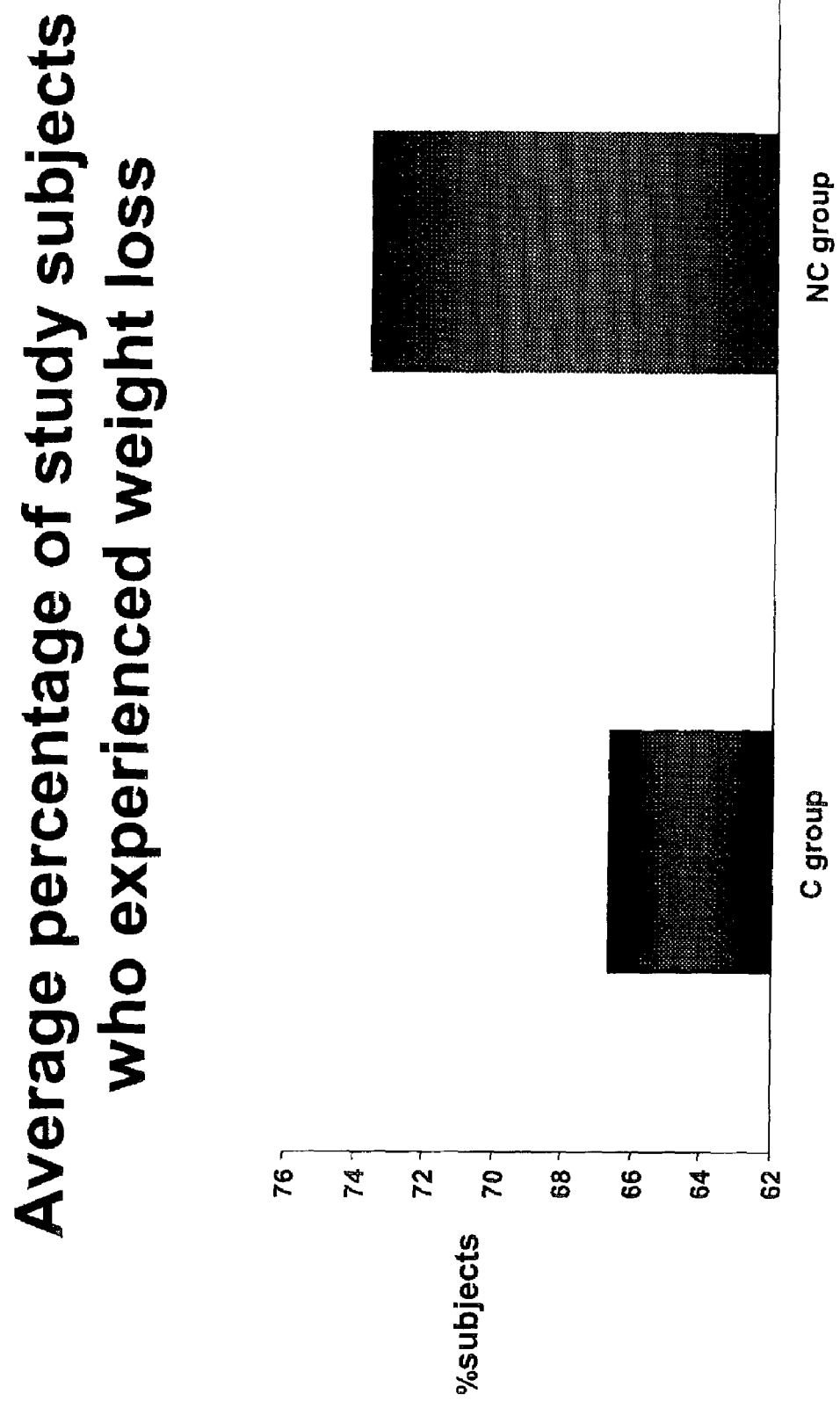
FIG. 2: Average percentage of study subjects who experienced weight loss.
Figure 3:
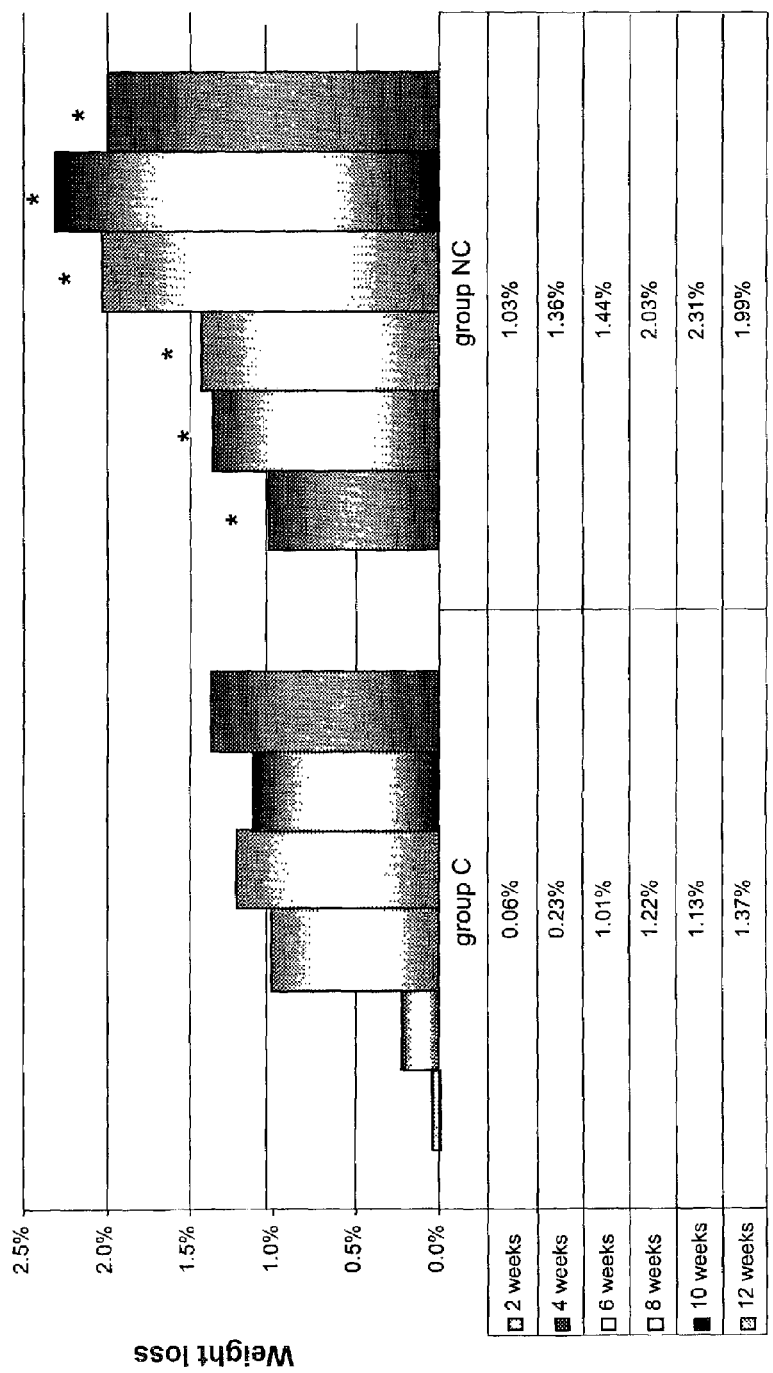
FIG. 3: Percentage of weight loss in groups C and NC in consecutive study time intervals.
Figure 4:
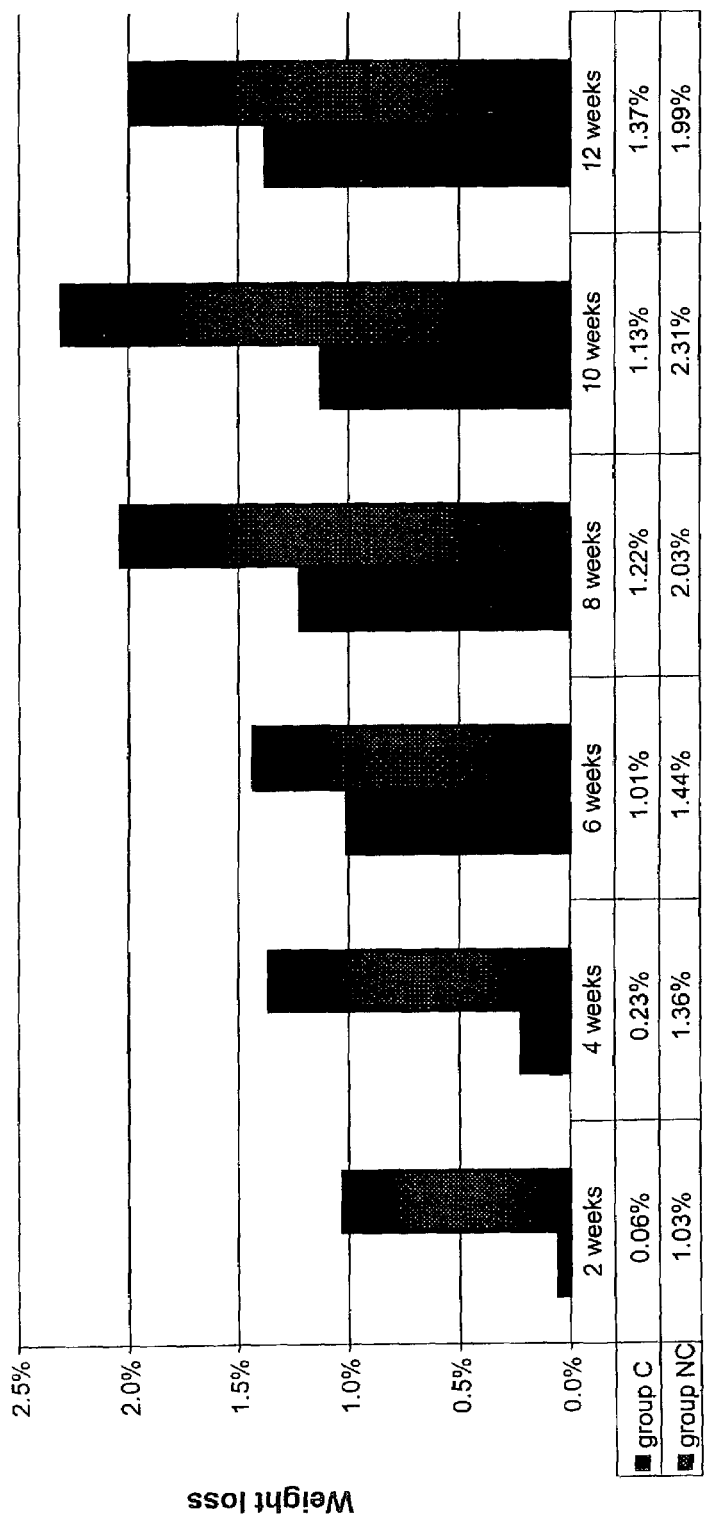
FIG. 4: Percentage of weight loss in group C and NC at consecutive study time intervals.
Figure 5:
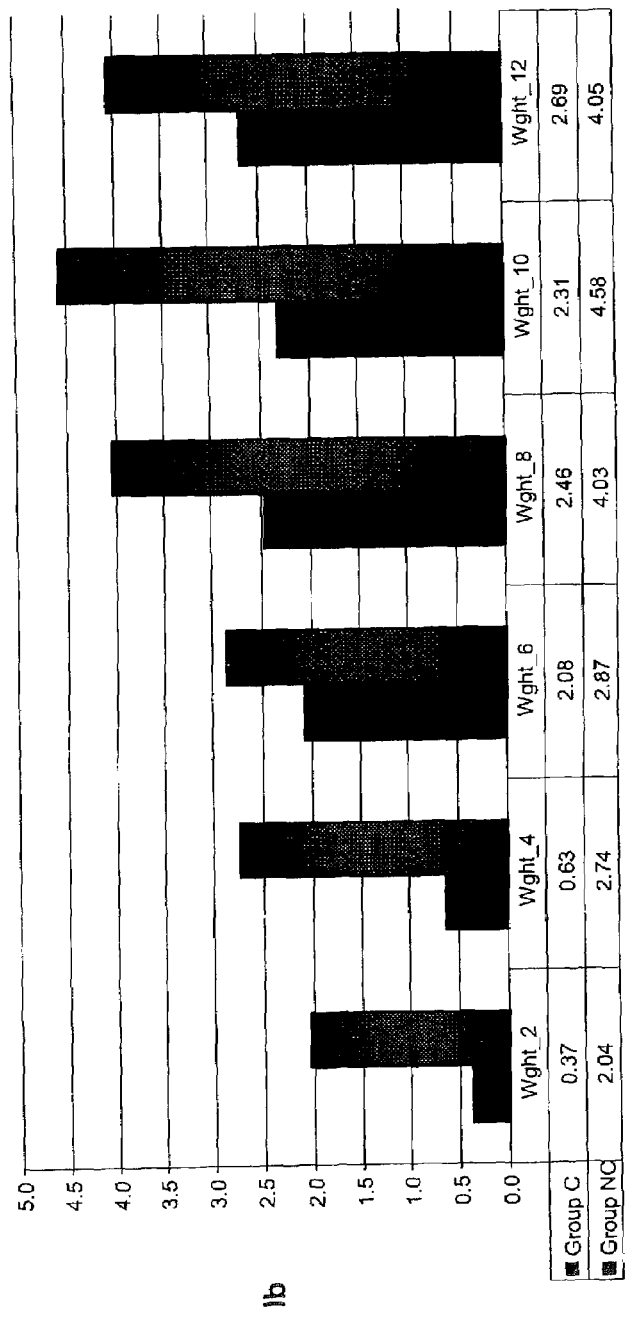
FIG. 5: Average weight loss (lbs) in group C and NC at consecutive study intervals.
Figure 6:
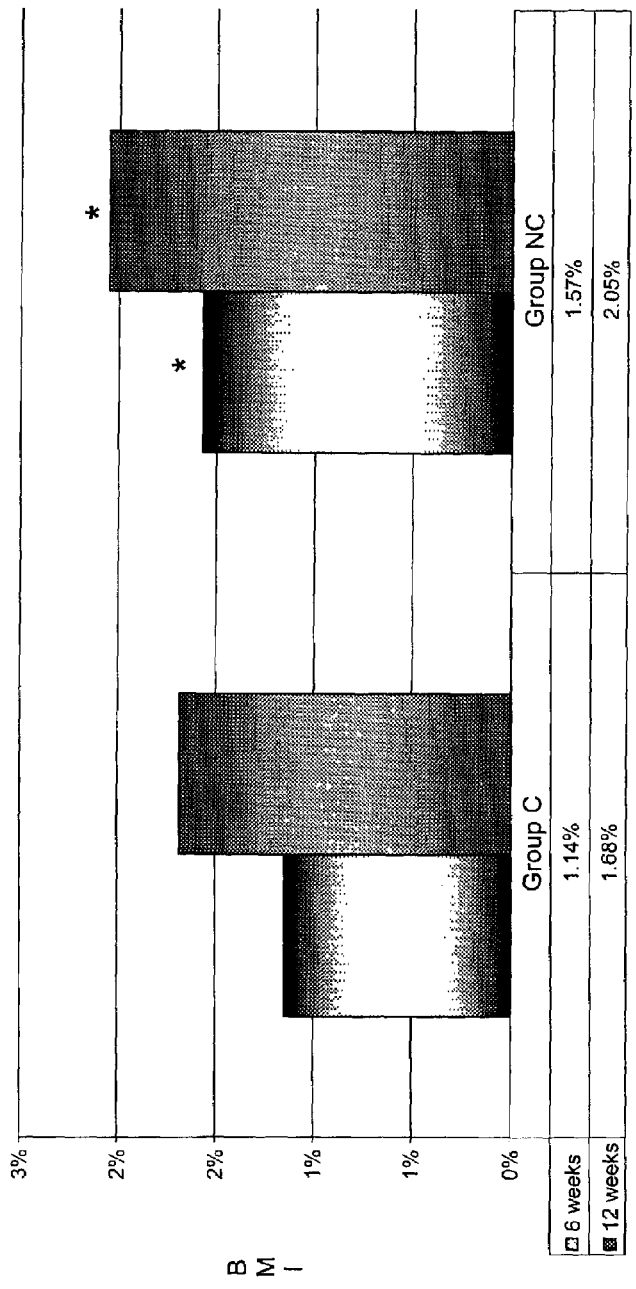
FIG. 6: Average percentage body mass index (BMI) change in groups C and NC at two study time intervals.
Figure 7:
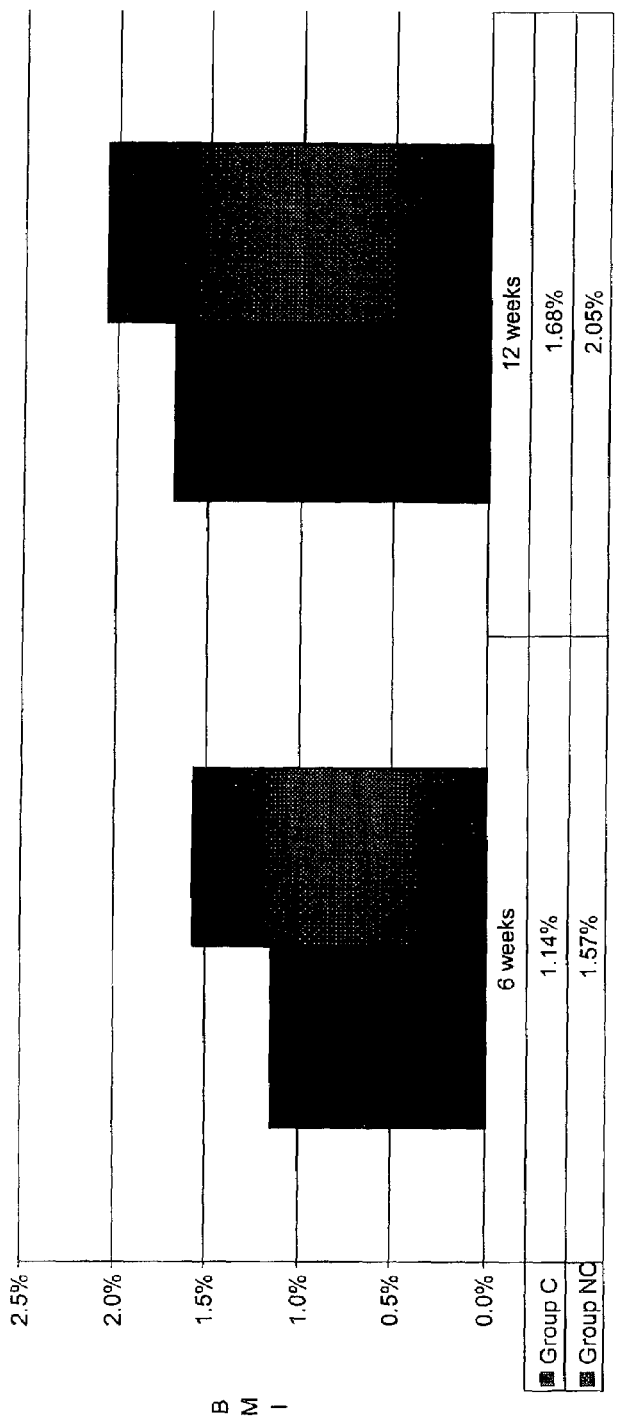
FIG. 7: Percentage of body mass index (BMI) change in group C and NC at two study time intervals.
Figure 8:
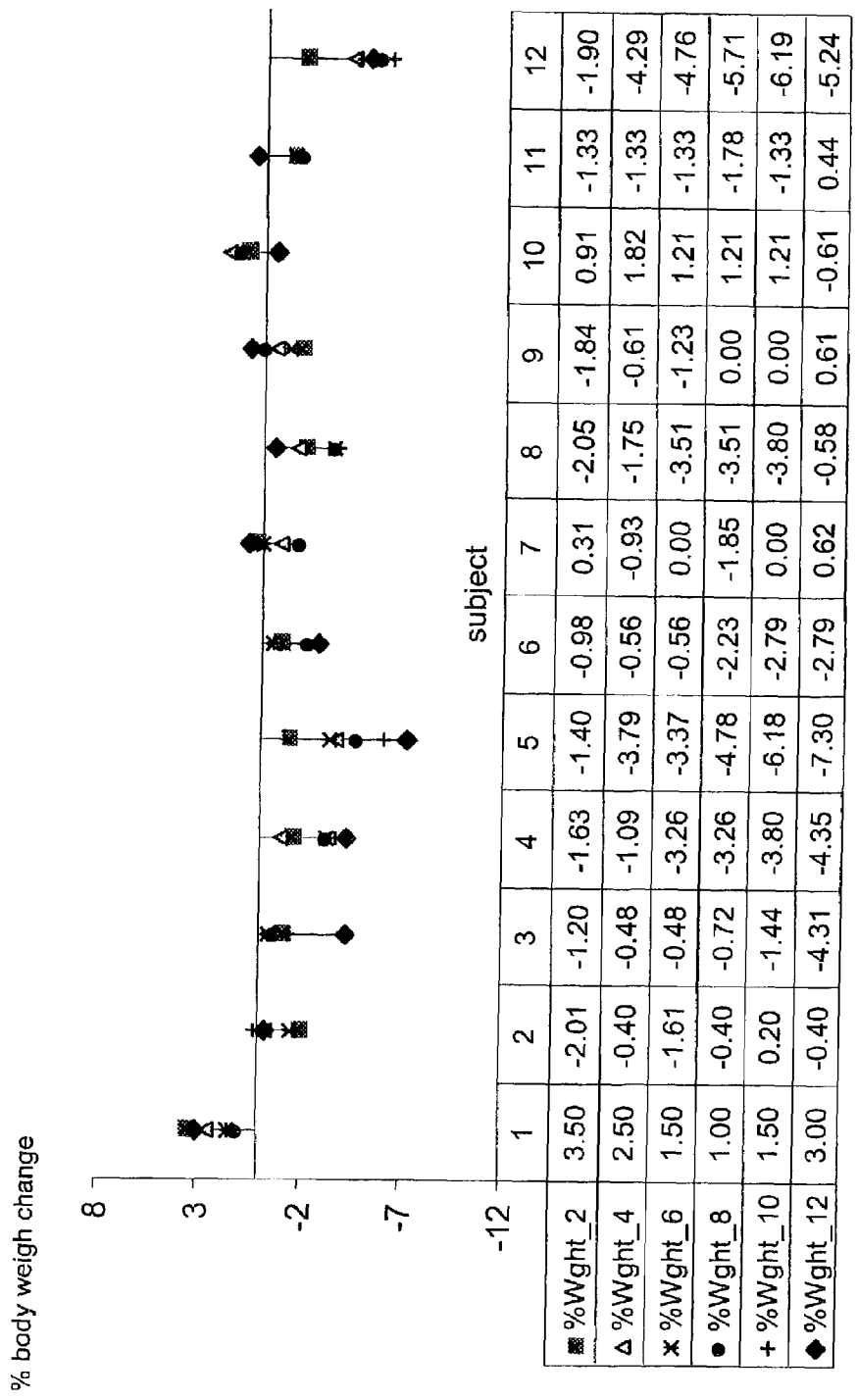
FIG. 8: Percentage body weight change in group C subjects.
Figure 9:
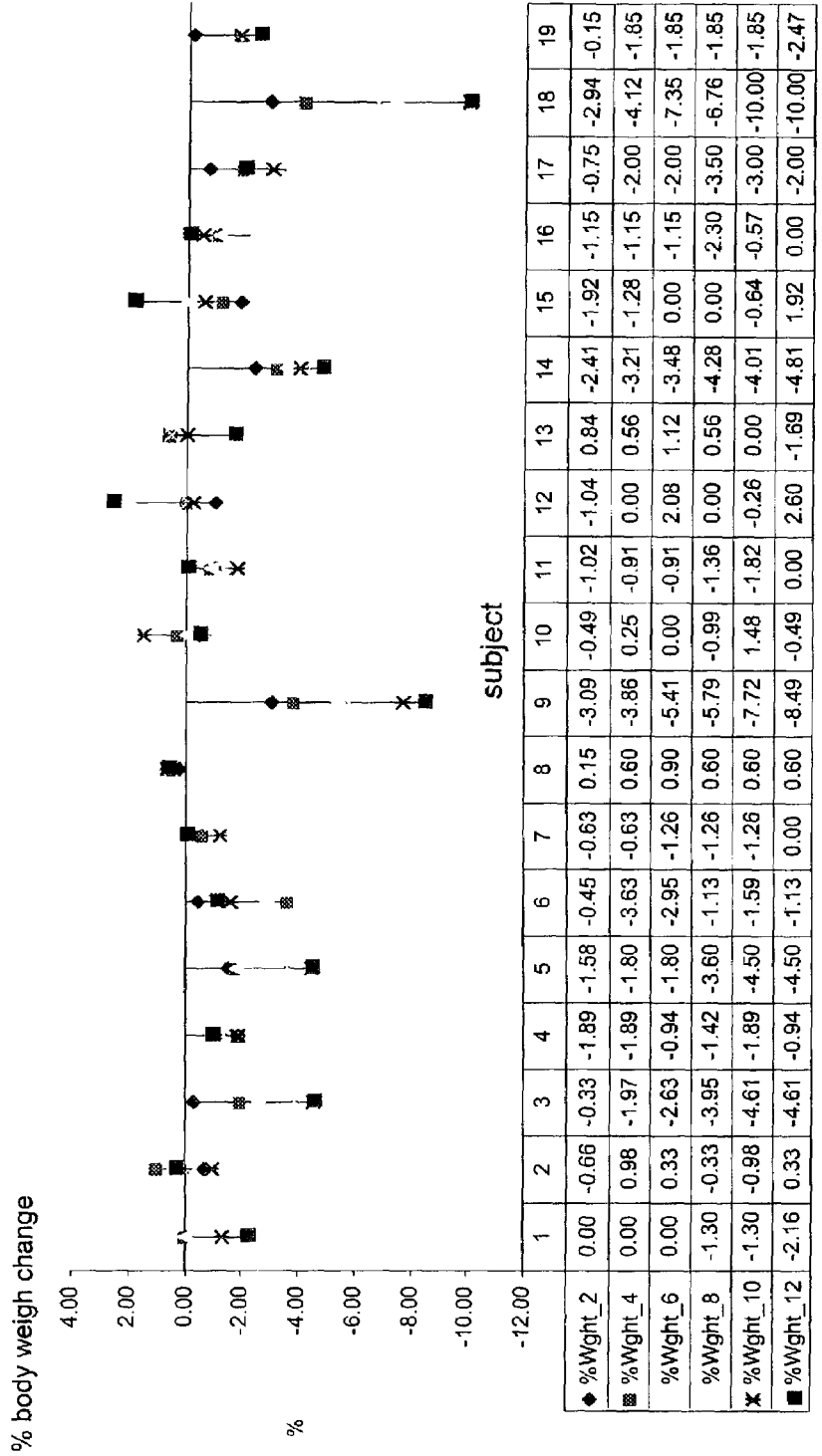
FIG. 9: Percentage body weight change in NC group subjects.
Figure 10:
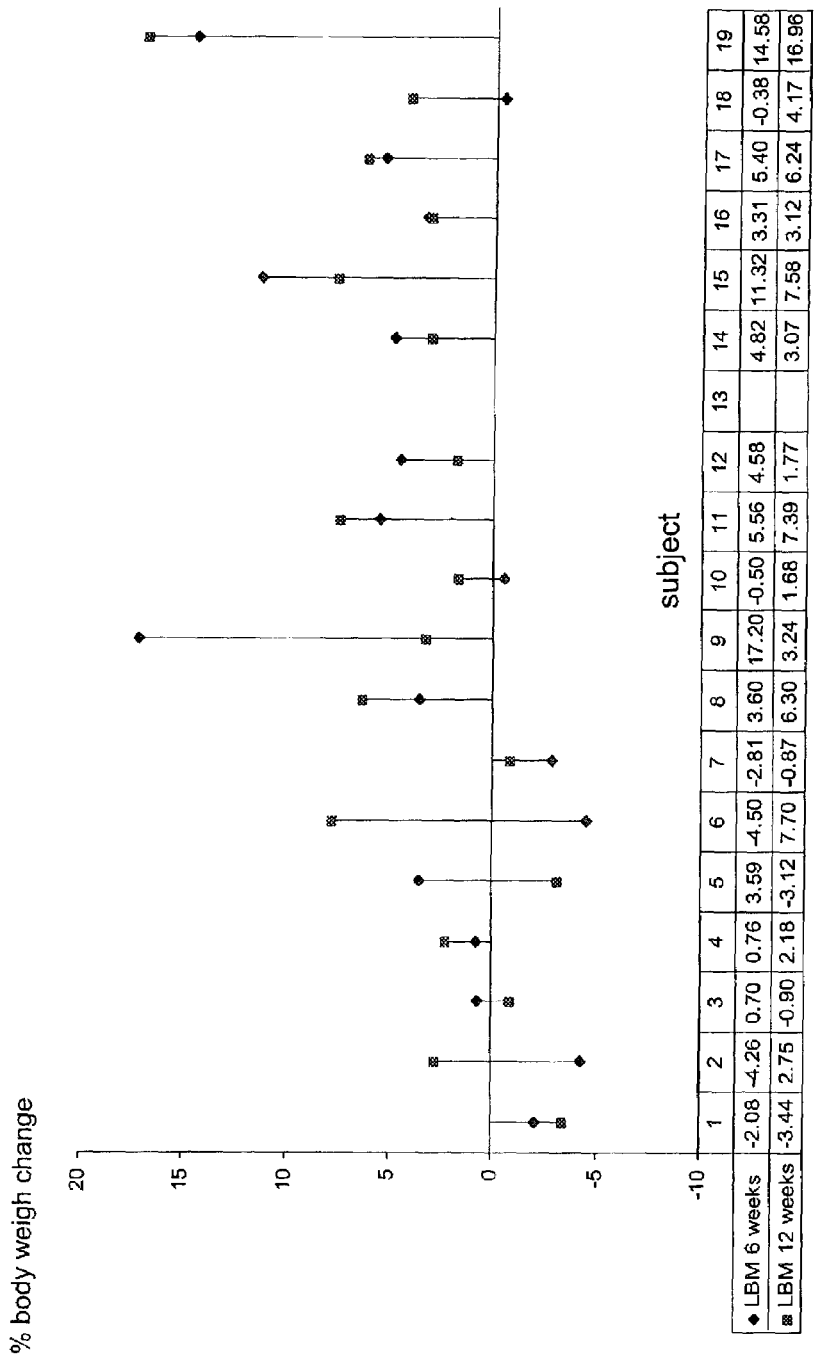
FIG. 10: Percentage lean body mass (LBM) change in group NC subjects.
Figure 11:
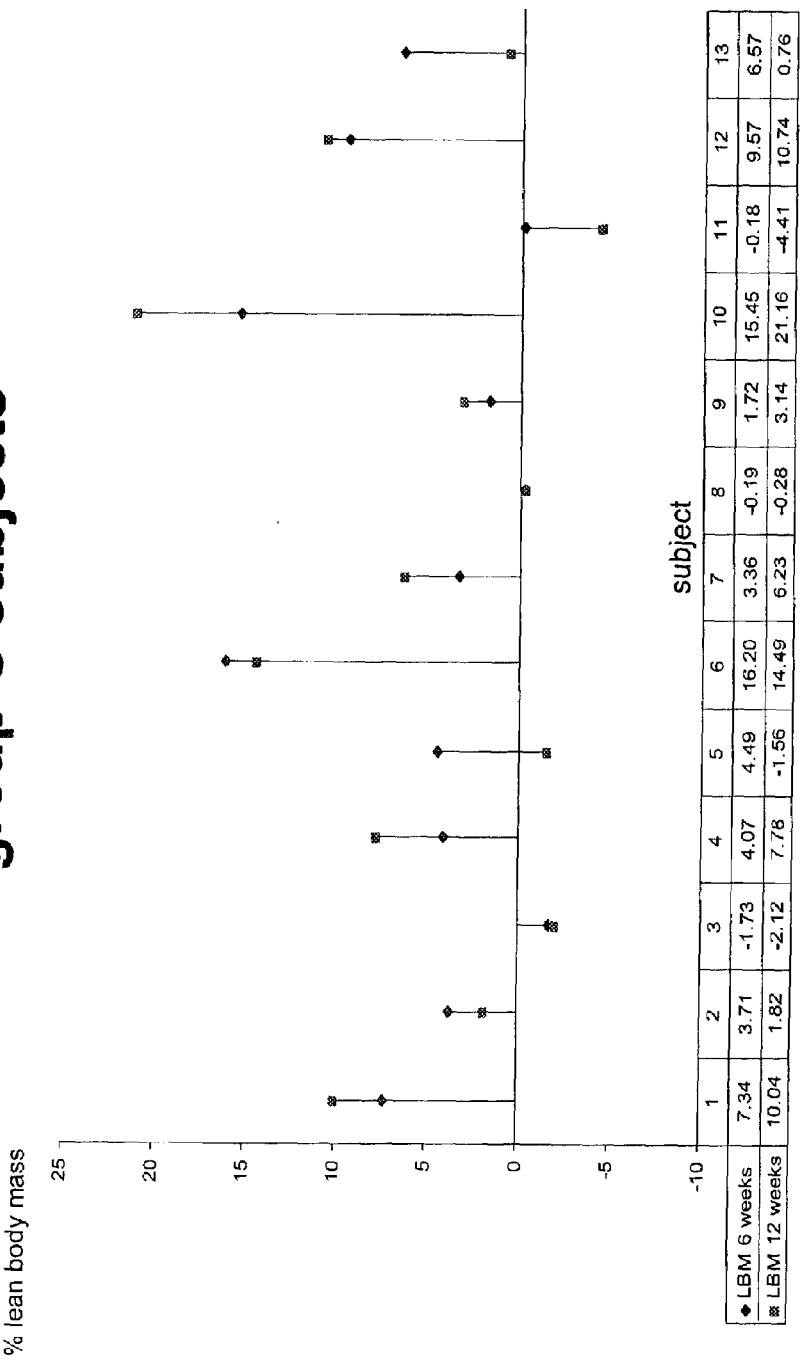
FIG. 11: Percentage lean body mass (LBM) change in group C subjects.
Figure 12:
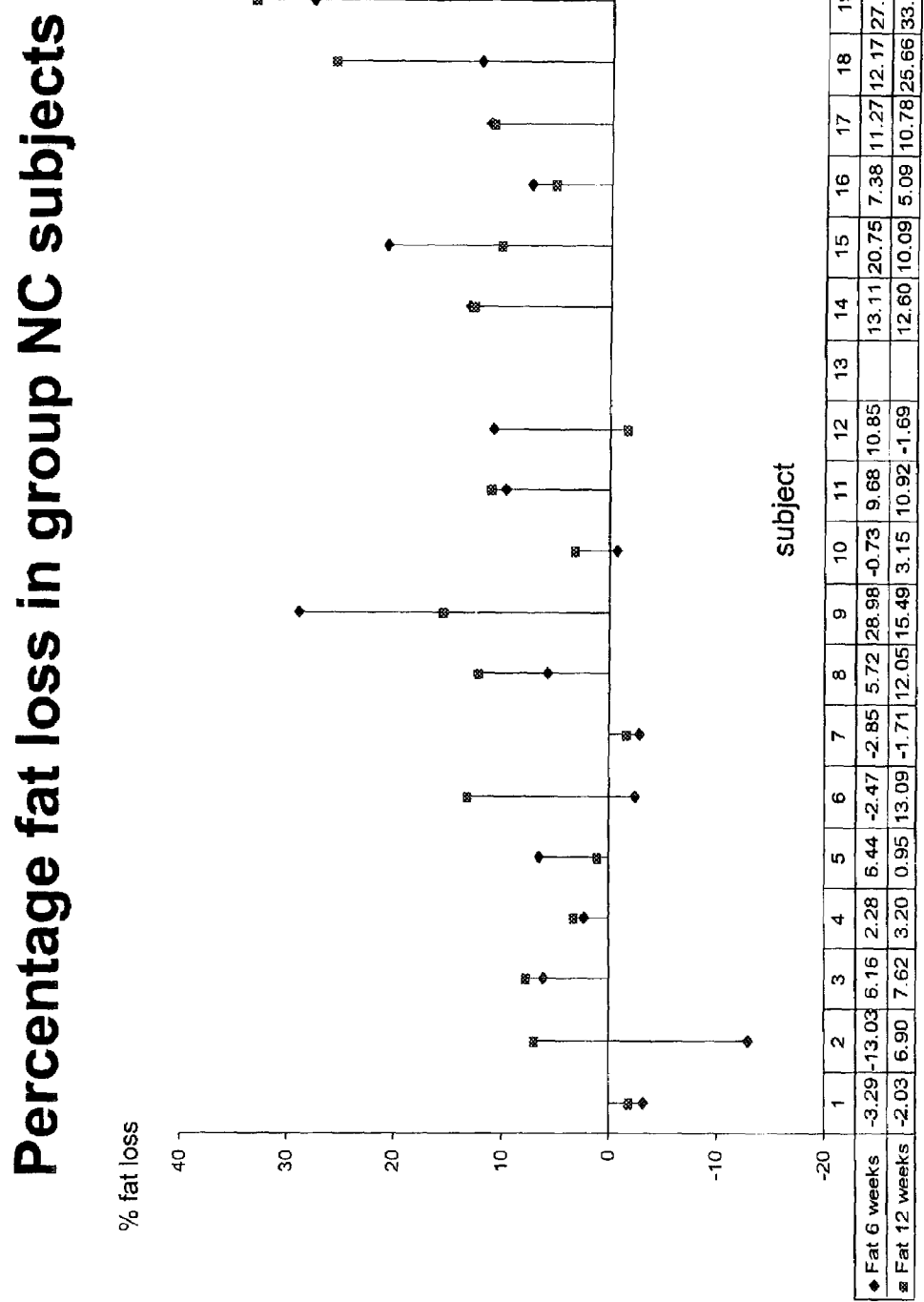
FIG. 12: Percentage fat loss in group NC subjects.
Figure 13:
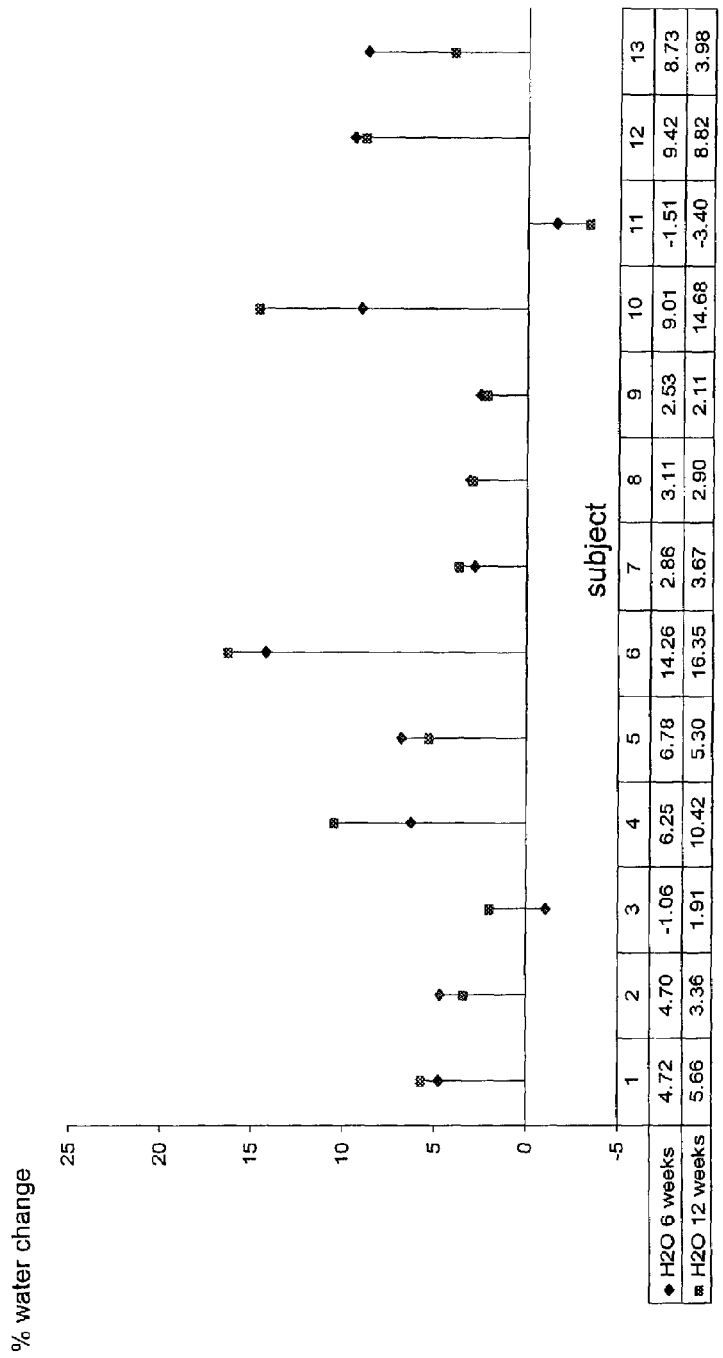
FIG. 13: Percentage water change in group C subjects.
Figure 14:
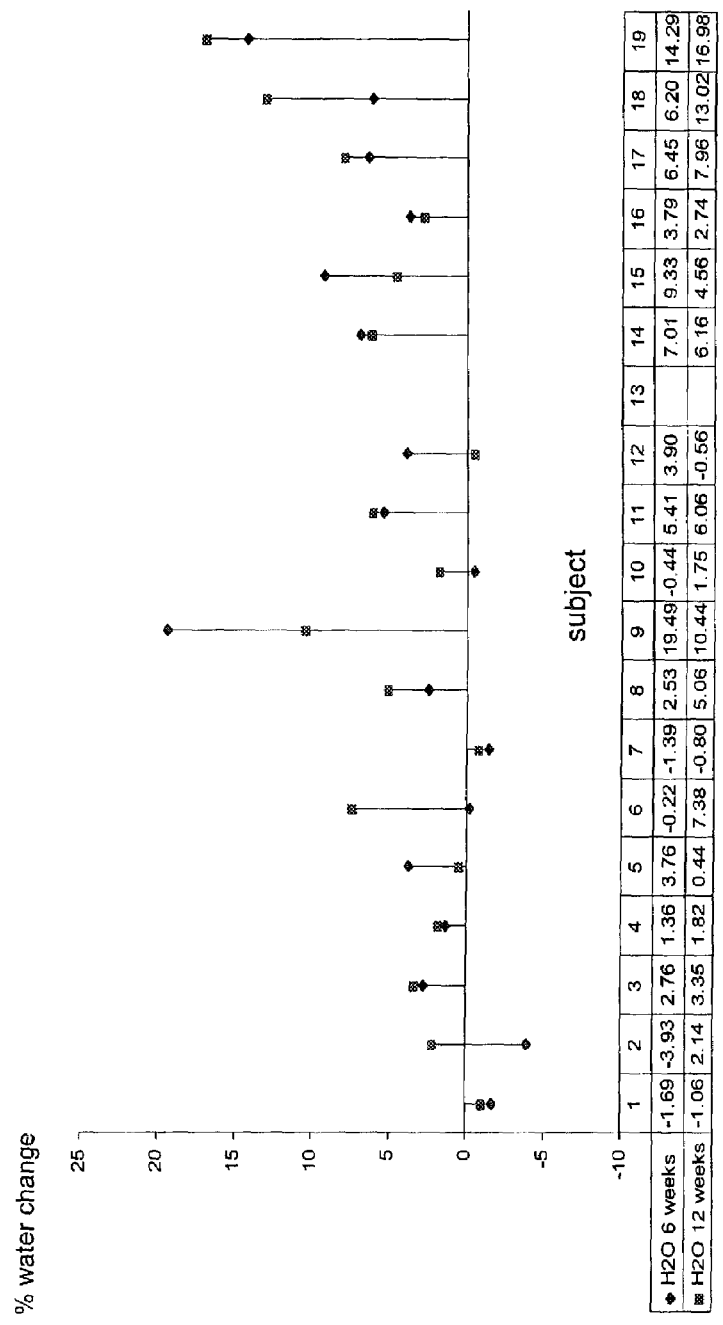
FIG. 14: Percentage water change in group NC subjects.
Figure 15:
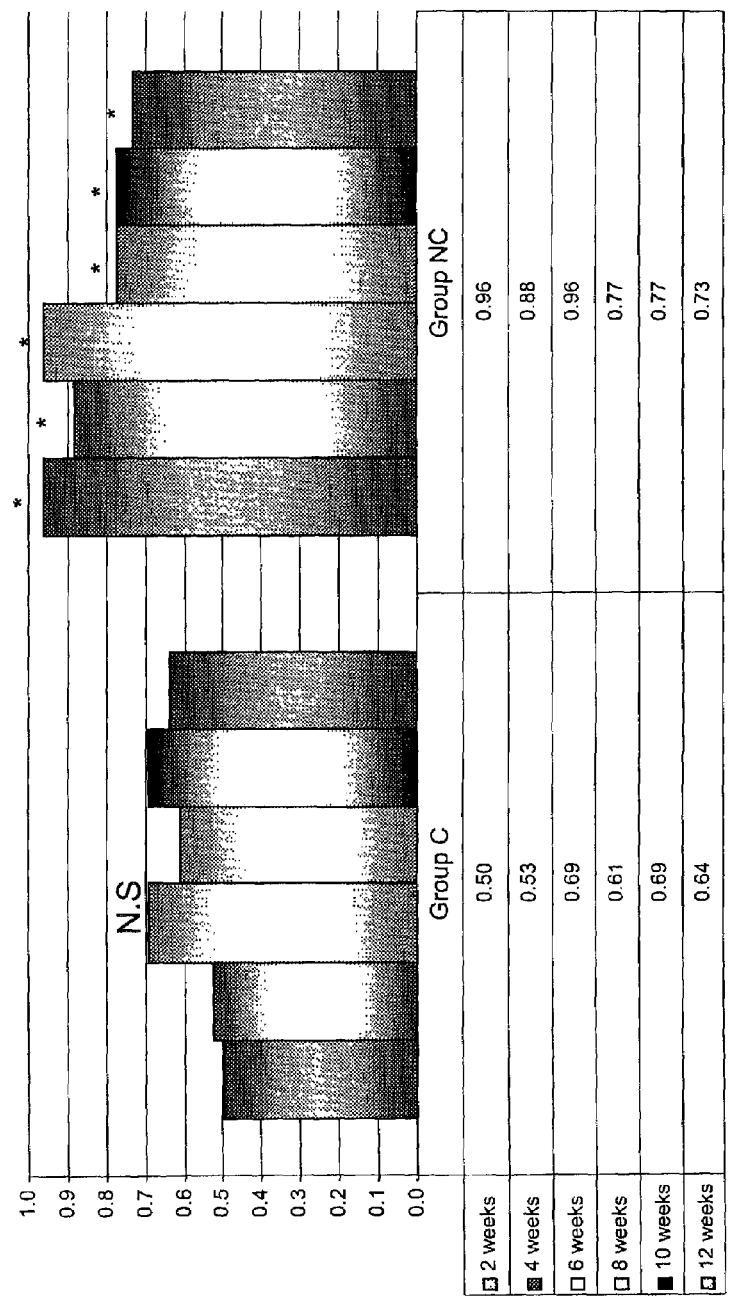
FIG. 15: Self assessed appetite levels in group C and NC in consecutive time intervals.
Figure 16:
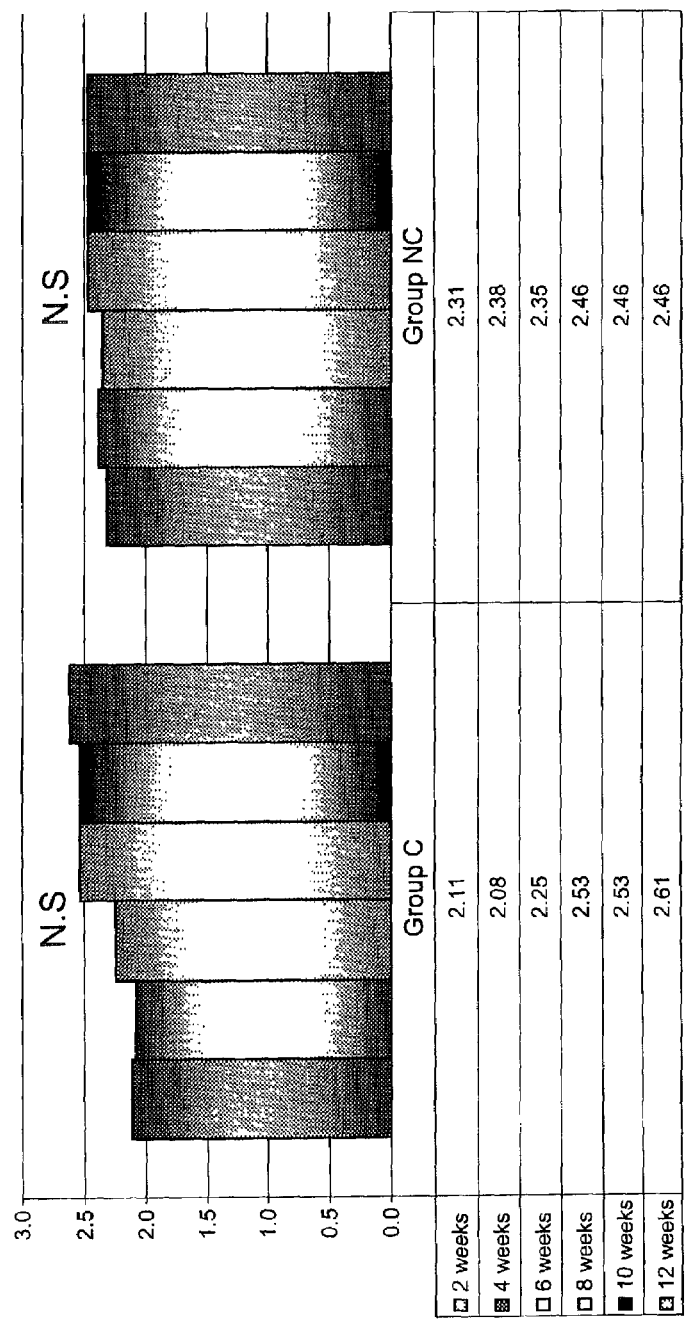
FIG. 16: Self assessed energy levels in groups C and NC in consecutive study time intervals.
Figure 17:
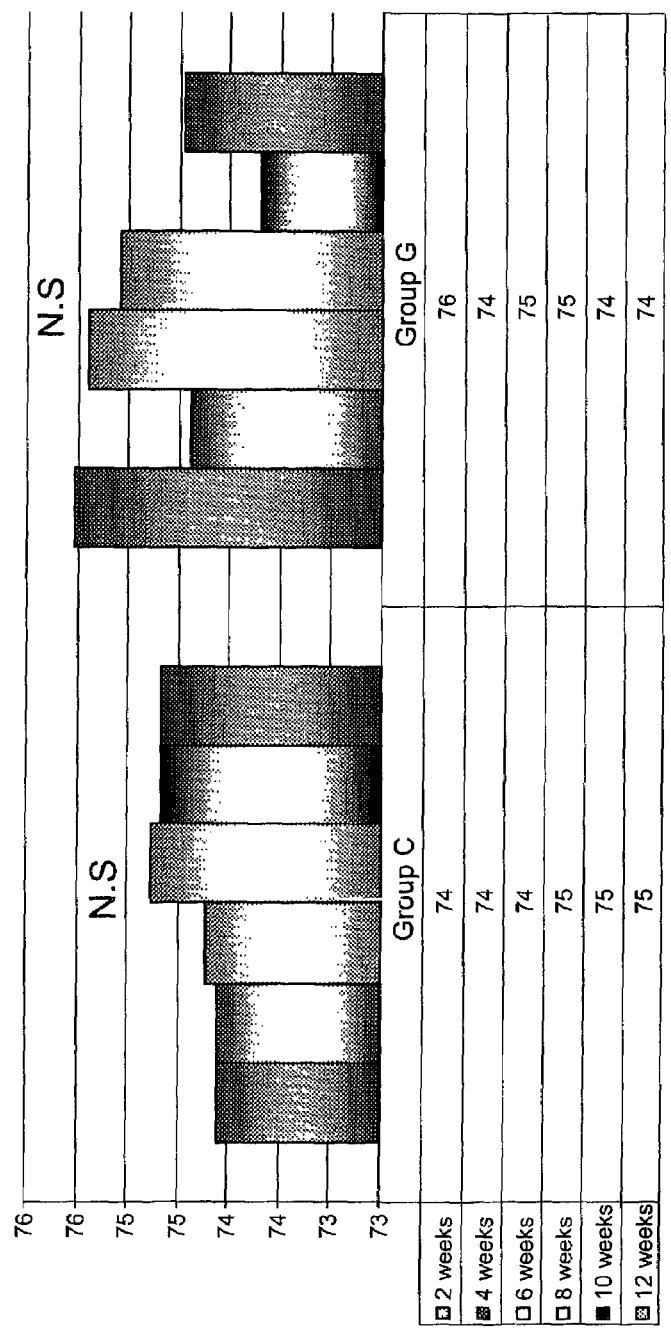
FIG. 17: Pulse rate in groups C and NC in consecutive time intervals.
Figure 18:
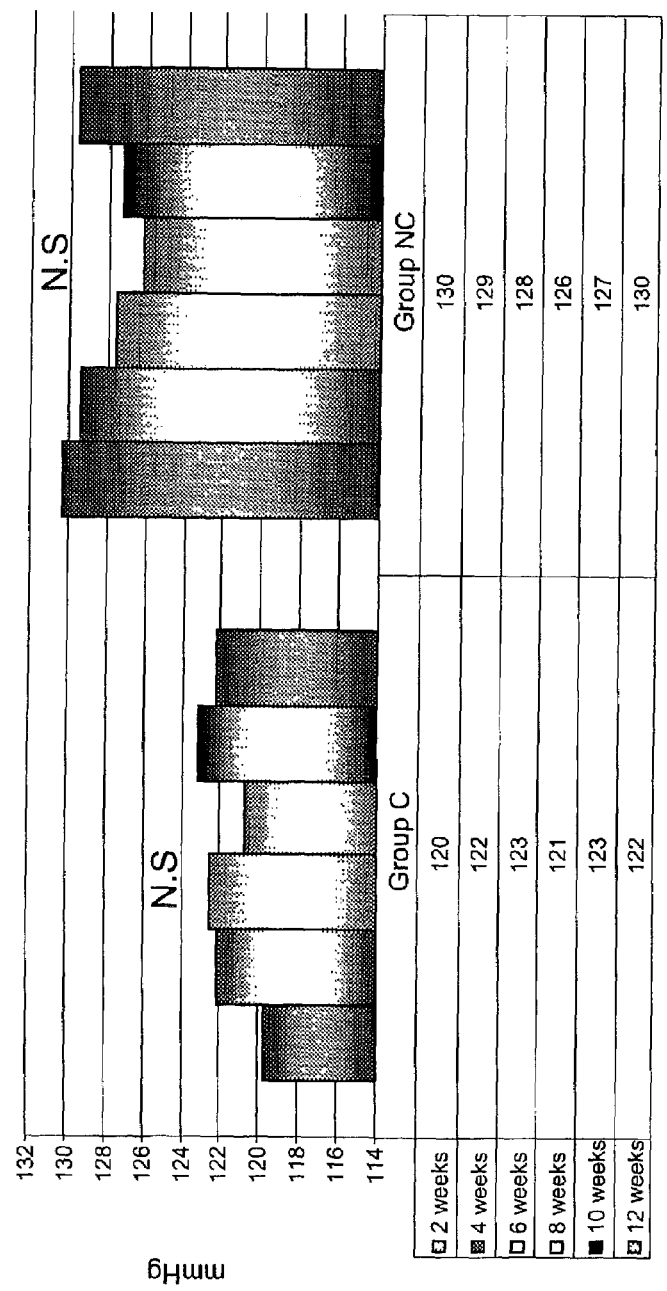
FIG. 18: Systolic blood pressure in groups C and NC in consecutive study time intervals.
Figure 19:
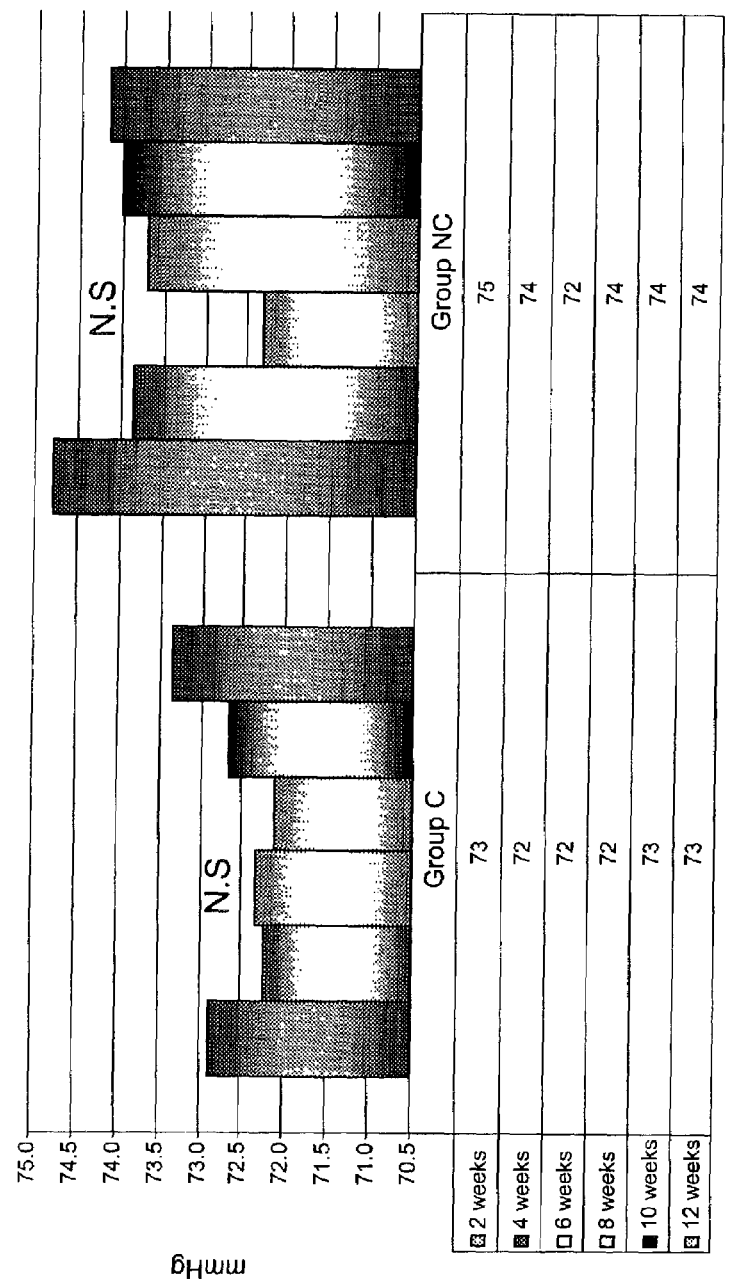
FIG. 19: Diastolic blood pressure in groups C and NC in consecutive study time intervals.

The invention relates to a composition comprising hydroxycitric acid (HCA) in combination with either one or both of garcinol and anthocyanin and having the effect of increasing bioavailability of HCA in the cytosolic compartment of a cell.

Another object of the present invention, involves the use of the inventive composition comprising HCA in combination with either one or both of garcinol and anthocyanin, as a weight-loss therapy in animal subjects, preferably humans. The therapeutic effects for the composition observed in murine and human studies include a reduction in total body weight and body mass index, a reduction in body fat, an increase in lean body mass and content of body water, and a reduction in perceived appetite level. The combination of the compounds is also shown to exert greater citrate lyase inhibiting properties than either compound alone.

Garcinol, alone, is also shown to have chemopreventive properties in an animal tumor model.

Biological activity includes but is not limited to activity for appetite suppression, inhibition of cytoplasmic citrate lyase, enhanced fat catabolism, and increased anti-oxidant activity.

Hydroxycitric acid (HCA) is an alpha-hydroxy tribasic acid (1,2-dihydroxy propane -1, 2, 3-tricarboxylic acid) comprising (−)hydroxycitric acid (I), (+) hydroxycitric acid (II), (−) allo-hydroxycitric acid (III), and (+) allo-hydroxycitric acid (IV).

Garcinol is a polyisoprenylated benzophenone (PPB) derived from *Garcinia* sp. Garcinol is a well-known antioxidant (i.e., emulsified garcinol suppressed superoxide anion comparably to DL alpha-tocopherol), anti-carcinogen and also has anti-microbial properties.

Anthocyanins are one class of flavenoid compounds, which are widely distributed plant polyphenols. There is considerable evidence that dietary anthocyanin pigments have preventative and therapeutic roles in a number of human diseases. The chemical basis for these desirable properties of anthocyanins is believed to be related to their antioxidant capacity—their ability to scavenge and trap free radicals that damage biomolecules.

The combination of garcinol and HCA enhances bioavailability of HCA in the cytosol and this same combination also enhances the antioxidant properties of garcinol. This mutual enhancement of the biological properties for the compounds of the invention, is referred to as "a biological effect amplification" or "Amplibio".

Amplibio refers to a mechanism wherein either one of the compounds serves to facilitate the biological effect of other compounds and as a result, both biological activities are enhanced.

In many biological systems, interaction of two or more components may result in no interaction, antagonism, synergism or a distinct form of synergism called amplibio. Not all compounds that exert synergism exert amplibio action. For example, there is an advantage in combining alpha lipoic acid with vitamins E and/or C, because lipoic acid recycles both vitamins, making them more bioavailable to the body. However, both vitamins do not enhance or otherwise improve the action of the lipoic acid. On the other hand, the results obtained by combining polyunsaturated fatty acids with fat soluble vitamins exemplifies an Amplibio effect: Vitamin E preserves fatty acids by preventing oxidation, while fatty acids enhance absorption of vitamin E. Another example of an Amplibio effect is observed when supplemental nutrients are combined with compounds endogenously produced by the living body: curcuminoids are known to enhance glutathione levels in the body, which occurs through regulating the rate of glutathione use in glutathione-free radical reaction. Elevated glutathione, in turn, increases the availability of curcuminoids in the body.

The Amplibio action of the present invention may involve the following mechanisms:

the anti-oxidant action of garcinol/anthocyanin (enhanced by HCA) neutralizing negative charges surrounding the cell to facilitate transport and uptake of HCA into the cell;

garcinol/anthocyanin affecting fluidity of cell membranes to facilitate transport and uptake of HCA into the cell;

garcinol/anthocyanin synergizing with HCA to inhibit citrate lyase, thus lowering the threshold for such inhibition with the HCA.

Therefore, enhancement of HCA activity is shown to be effected by its interaction with garcinol/anthocyanin, likewise, HCA is observed to enhance the biological potential of garcinol and anthocyanin. The qualitative and quantitative interaction among the three compounds of the invention have not been described previously.

Methods for extracting and purifying HCA, garcinol and anthocyanin compounds are well known in the art.

The present invention also includes a method of preparing a composition comprising PPB, anthocyanin and HCA extracted from fruits of *Garcinia* sp., the method comprising:

(a) extracting the fresh fruits of *Garcinia* with 8 to 1 5 parts of C1 to C6 alcohol (e.g. methanol, ethanol, isopropyl alcohol) by refluxing and circulating in a closed reactor until extraction is completed;

(b) filtering the extracted material from the spent material;

(c) concentrating the extracted material to ¼–⅙ its volume under vacuum at 540 to 600 mm/Hg;

(d) chilling the concentrate for approx. 20 to 30 hours at −5 to 5° C. and filtering the precipitated material in a Nutsche filter;

(e) obtaining a solid residue (yield 2.5 to 4%) comprising crude Garcinol (Assay 16–20%).

(f) dissolving crude Garcinol extract in a hydrocarbon solvent such as petroleum ether, hexane or toluene (3 to 8 parts), and extracting/partitioning with a high polar, non-miscible solvent such as acetonitrile (2 to 4 parts, 3 to 5 times);

(g) separating and concentrating the polar solvent layer to ¼–⅙ its volume, and chilling at −5 to 8° C. for 12 to 16 hours;

(h) filtering and washing the residue with the polar solvent to obtain yellow Garcinol (yield=0.8 to 1.5%, Assay 55 to 70%);

(i) adding to the extracted material of step c), molar equivalent quantities of alkali (sodium hydroxide or potassium hydroxide) calculated on the basis of the content of HCA (about 20 to 25%);

(j) heating the mixture under stirring at 80 to 95° C. for 2.5 to 5 hours to obtain yellow PPB (Garcinol);

(k) filtering the precipitated material (HCA salt of sodium or potassium) using a Nutsche filter and washing with cold alcohol;

(l) dissolving the precipitated material in 3 to 5 parts of water;

(m) adding to this aqueous solution, molar equivalent quantity of calcium chloride and heating with stirring at 80 to 95° C. for 4 to 6 hours;

(n) filtering and drying the precipitated material at 50 to 75° C. under vacuum to obtain white HCA calcium (yield=25 to 35%);

(o) blending the yellow PPB (Garcinol) powder obtained in step (j) and the HCA calcium obtained in step (n) at a ratio of 1:10 to yield a composition containing HCA calcium at a minimum of 55% and PPB (Garcinol) at a minimum of 5%; and (p) optionally blending HCA calcium or any other salt of HCA, with PPB and proantho-cyanidins in effective proportions at a minimum of 0.5% of the proanthocyanidins.

The PPB composition of the invention can also be obtained as follows:

(a) extracting *Garcinia* spent fruit from suspension with toluene and 5% methanol to obtain a paste having 20% PPB's (Garcinol—15%; Cambogin—5%);

(b) upgrading the paste to obtain a composition comprising 50% Garcinol and approx. 10–15% Cambogin which comes in the mother liquor, and 50% Garcinol is upgraded further by one more crystallization to yield 90% Garcinol plus 35% cambogin;

(c) heating a 90% Garcinol composition to 100° C. for conversion to Cambogin of about 80% proof, the reminder being Garcinol;

(d) mixing the product of step (c) in equal proportion with part of a 90% Garcinol composition to obtain a 85%–90% PPB composition with 42–45% proof;

(e) obtaining a final composition with a 90% PPB in almost equal proportion to Cambogin and Garcinol, the remainder being cyclised products called poly isoprenylated xanthones.

The term "bioavailability" is defined as any means to enhance the effective mechanism of a weight loss compound. By analogy, the bioavailability of calcium in the body is ultimately measured by increased bone mass, which means that any mechanism serving the purpose of incorporating the supplemental calcium in the bone will increase bioavailability of calcium.

The term "effective amount" means a sufficient amount of compound, e.g. corresponding to HCA, garcinol or anthocyanin delivered to produce an adequate level of cytosolic citrate lyase.

A primary object of the invention is to provide a method of therapy where the bioavailability of HCA is dramatically increased to obtain therapeutically effective amounts of HCA in the cytosol, thereby treating the subject in need of reducing or inhibiting citrate lyase. This enhanced activity for HCA is achieved by co-administration with compounds including but not limited to garcinol and anthocyanin.

Another object of the invention is to provide a method of weight-loss therapy where the effects of forskolin (U.S. Pat. No. 5,804,596) are dramatically increased by the presence of garcinol and, optionally, anthocyanin. The amount of forskolin is the same as taught in the '596 patent, and the amounts of garcinol and anthocyanin are the same as taught herein for use with HCA.

More specifically, a weight loss and appetite suppressing effective amount of HCA and garcinol is 500 mg tid and 25 mg respectively, more preferably the dose of garcinol can range from 0.01% to 10% of the HCA or other weight loss compounds like diterpene forskolin (U.S. Pat. No. 5,804,596). A weight loss effective amount of HCA and anthocyanin is 500 mg tid and 10 mg respectively, more preferably the dose of anthocyanin can range from 0.01% to 10% of the HCA or other weight loss compounds like diterpene forskolin (U.S. Pat. No. 5,804,596). A weight loss and appetite suppressing effective amount of HCA, garcinol and anthocyanin is 500 mg, 25 mg and 10 mg respectively, more preferably the dose of garcinol and anthocyanin can range from 0.01% to 10% of the HCA or other weight loss compounds like diterpene forskolin (U.S. Pat. No. 5,804, 596).

A citrate lyase inhibiting effective amount of HCA and garcinol is 500 mg tid and 25 mg respectively, more preferably the dose of garcinol can range from 0.01% to 10% of the HCA or other weight loss compounds like diterpene forskolin (U.S. Pat. No. 5,804,596). A citrate lyase inhibiting effective amount of HCA, and anthocyanin is 500 mg tid and 10 mg respectively, more preferably the dose of anthocyanin can range from 0.01% to 10% of the HCA or other weight loss compounds like diterpene forskolin (U.S. Pat. No. 5,804,596). A citrate lyase inhibiting effective amount of HCA, garcinol and anthocyanin 500 mg, 25 mg and 10 mg respectively, more preferably the dose of garcinol and anthocyanin can range from 0.01% to 10% of the HCA or other weight loss compounds like diterpene forskolin (U.S. Pat. No. 5,804,596).

A fat catabolizing and lean body mass enhancing effective amount of HCA and garcinol is 500 mg tid and 25 mg respectively, more preferably the dose of garcinol can range from 0.01% to 10% of the HCA or other weight loss compounds like diterpene forskolin (U.S. Pat. No. 5,804, 596). A fat catabolizing and lean body mass enhancing effective amount of HCA and garcinol is 500 mg tid and 25 mg respectively, more preferably the dose of garcinol can range from 0.01% to 10% of the HCA or other weight loss compounds like diterpene forskolin (U.S. Pat. No. 5,804, 596). A fat catabolizing and lean body mass effective amount of HCA, garcinol and anthocyanin is 500 mg, 25 mg and 10 mg respectively, more preferably the dose of garcinol and anthocyanin can range from 0.01% to 10% of the HCA or other weight loss compounds like diterpene forskolin (U.S. Pat. No. 5,804,596).

The therapeutic weight-loss effects of HCA and garcinol, in combination, and the role of garcinol as chemopreventive agent are described by way of the following non-limiting examples.

EXAMPLE 1

Administration of garcinol and HCA to two strains of mice, SKH-1 and CF-1 respectively, resulted in significantly less total body weight and abdominal fat gain, as compared to control, chow-receiving animals and the groups of animals receiving either garcinol or HCA alone. In addition, dietary administration of garcinol caused significant reduction in aberrant colonic crypt formation (AC is considered a pre-malignant condition) in CF-1 mice as compared to the animals fed control diet or diet containing HCA or garcinol alone. Interestingly, the weight-gain preventive effect of garcinol and HCA combination was accomplished despite that the garcinol plus HCA animals had higher food and water consumption than the control, garcinol and HCA groups.

TABLE 1

Effect of oral administration of garcinol (GAR), hydroxycitric acid (HCA) and combination of garcinol and hydroxycitric acid on body weight, food and fluid consumption in SKH-1 mice

| Group | 5 weeks | 7 weeks | 10 weeks |
|---|---|---|---|
| Body weight (gm; Mean ± SE) | | | |
| 1. Control | 32.3 ± 0.67 | 34.5 ± 0.99 | 37.0 ± 1.49 |
| 2. 0.05% GAR | 32.8 ± 0.37 | 33.9 ± 0.14 | 36.4 ± 0.55 |
| 3. 1% HCA | 32.5 ± 0.42 | 34.5 ± 0.59 | 36.8 ± 0.33 |
| 4. (2) + (3) | 31.2 ± 0.20 | 33.5 ± 0.58 | 34.9 ± 0.88 |
| Food consumption (gm/mouse/day; Mean ± SE) | | | |
| 1. Control | 5.25 ± 0.33 | 5.09 ± 0.28 | 5.16 ± 0.25 |
| 2. 0.05% GAR | 4.98 ± 0.17 | 5.09 ± 0.46 | 5.26 ± 0.17 |
| 3. 1% HCA | 5.74 ± 0.13 | 6.49 ± 0.07 | 6.93 ± 0.21 |
| 4. (2) + (3) | 6.55 ± 0.20 | 8.03 ± 1.45 | 9.31 ± 1.12 |
| Water consumption (ml/mouse/day; Mean ± SE) | | | |
| 1. Control | 3.75 ± 0.04 | 3.42 ± 0.34 | 3.80 ± 0.22 |
| 2. 0.05% GAR | 3.66 ± 0.07 | 3.63 ± 0.05 | 3.73 ± 0.17 |
| 3. 1% HCA | 3.72 ± 0.08 | 3.74.5 ± 0.04 | 3.84 ± 0.09 |
| 4. (2) + (3) | 3.68 ± 0.08 | 3.86 ± 0.08 | 3.94 ± 0.08 |

TABLE 2

Effect of 10 week oral administration of garcinol (GAR) and hydroxycitric acid (HCA) on azoxymethane (AOM)-induced formation of aberrant colonic crypts (AC) and accumulation of fat in abdomen in CF-1 mice

| Group | Body weight (gm) | AC per colon | parametrial fat (gm) | retroperitoneal fat (gm) |
|---|---|---|---|---|
| 1. Control | 38.8 ± 1.52 | 11.4 | 1.33 ± 0.19 | 0.95 ± 0.11 |
| 2. 0.05% GAR | 37.3 ± 1.07 | 7.8 (31.6%) | 1.21 ± 0.18 | 0.85 ± 0.01 |
| 3. 1% HCA | 37.9 ± 0.66 | 7.9 (30.7%) | 1.24 ± 0.06 | 0.79 ± 0.04 |
| 4. (2) + (3) | 36.1 ± 0.48 | 8.5 (25.4%) | 0.95 ± 0.10 | 0.70 ± 0.13 |

These data suggest a broad biological mechanism for garcinol as an adjuvant to HCA involving regulation of body weight, body composition and body metabolic rate.

EXAMPLE 2

The role of garcinol as a chemopreventive agent has been confirmed in an experiment in which CF-1 mice were treated topically with the inflammation and tumor promoting agent, TPA.

TABLE 3

Effects of garcinol (GAR) on TPA-induced ear edema*

| Treatment | Number of mice | Weight per punch (gm) | Percent Inhibition (%) |
|---|---|---|---|
| 1. TPA (1 nmol) | 5 | 15.5 ± 0.82 | — |
| 2. TPA + GAR (0.1 umol) | 4 | 12.4 ± 0.81 | 38.5 |
| 3. TPA + GAR (0.5 umol) | 4 | 9.25 ± 0.66 | 77.5 |

*Female CF-1 mice were treated topically with TPA applied to ear's skin with or without garcinol. Five hours later, the mice were killed and ear punches were weighted. Data are expressed as the mean ± SE.

These data suggest a biological mechanism for garcinol as a chemopreventative agent.

EXAMPLE 3

Clinical Studies on Weight-Loss Potential of Garcinol and HCA

The combination consisting of 500 mg of calcium salt of HCA and 25 mg of garcinol (NC) was evaluated in a double-blind, 12 week clinical study against the formula containing 500 mg of calcium salt HCA (C). The study was performed on 46 overweight female volunteers (BMI greater than 25). Participants were instructed to take one capsule of either active-containing or placebo formula three times a day, half an hour before a meal. Each participant was asked to maintain her previous daily physical exercise and eating habits. In addition, physical activity was monitored based on a questionnaire before and during the trial. The participants were evaluated at the baseline, weeks 2, 4, 6, 8, 10 and 12. The following clinical parameters were evaluated at each visit: total body weight, body composition by the bioelectric impedance method, self-assessed appetite and energy levels, pulse rate and blood pressure. During the 12 week trial, the mean values in group NC for body weight and fat content significantly decreased, whereas lean body mass and total body water significantly increased compared to the baseline values and C group values. The appetite levels were significantly less in the NC group than the C group, whereas energy levels were equally increased in both study groups as compared to the baseline. No subjective or objective adverse effects were reported in the course of this study. The pulse rate, systolic and diastolic blood pressure were maintained at the same level throughout the study.

NC is statistically more effective than C in reducing total body weight and body mass index; reducing body fat; increasing lean body mass and content of body water; and reducing levels of appetite perception. The energy levels of subjects were not enhanced by regimens in both groups, and NC and C did not produce subjective or objective side effects.

INDUSTRIAL APPLICATIONS

The combined data from animal and clinical studies indicate that the invention is more effective than HCA alone weight-loss therapy, and that in addition to fat loss, the inventive composition invention also improves lean body mass leading to improved body composition. Maintaining or improving lean body mass while shedding extra pounds of adipose tissue has been advocated by the Centers for Disease Control. Lean body mass is important because it has been recently recognized as an independent, positive predictor of one's cardiovascular health and overall health. The chemopreventive action of garcinol in the animal experimental model may also be intricately related to the role the compound has in improving body composition.

REFERENCES

1. Sullivan A C, Singh M, Srere P A, Glusker J P. Reactivity and Inhibitor Potential of Hydroxycitrate Isomers with Citrate Synthase, Citrate Lyase, and ATP Citrate Lyase. *J Biol Chem.* 1977; 252(21): 7583–7590.
2. Majeed M, Rosen R, McCarthy M, Conte A A, Patil D, Butrym E. Citrin A Revolutionary Herbal Approach to Weight Management. New Editions Publishing. Burlingame, Calif. 1994.
3. Sullivan A C, Hamilton J G, Miller O N, Wheatley. Inhibition of lipogenesis in rat liver by (–)-hydroxycitrate. *Arch Biochem Biophys.* 1972; 150: 183–190.
4. Sullivan A C, Triscari J, Hamilton J G, Miller O N. Effect of (–)-Hydroxycitrate upon the Accumulation of Lipid in the Rat: I. Lipogenesis. *Lipids.* 1973; 9(2):121–128.
5. Vasselli J R, Shane E, Boozer C N, Heymsfield S B. *Garcinia* Cambogia Extract Inhibits Body Weight Gain Via Increased Energy Expenditure (EE) In rats. *FASEB J.* 998;12(part1):A506.
6. Sullivan A C, Triscari J, Hamilton J G, Miller O N. Effect of (–)-Hydroxycitrate upon the Accumulation of Lipid in the Rat: II. Appetite. *Lipids.* 1973;9(2):121–128.
7. Conte A. A. A Non-Prescription Alternative in Weight Reduction Therapy. *The Bariatrician.* 1993: 17–19.
8. Conte A. A. The effects of (–)-Hydroxycitrate And Chromium (GTF) On Obesity. *J Amer Coll Nutr.* 1994 (October);13 (5): 535 [Abstract 60].
9. Katts G R, Pullin D, Parker L K, Keith P L, Keith S. Reduction Of Body Fat As A Function Of Taking A Dietary Supplement Containing *Garcinia* Cambogia Extract, Chromium Picolinate And L-Carnitine—A Double Blind Placebo Controlled Study. Abstract/Poster presented at a symposium on obesity organized by the Mexican Sociedad Medical del Sureste para el Estudio de la Obesidad, Mar. 4, 1995, Merida, Yucatan, Mexico.
10. Badmaev V, Majeed M. Open Field, Physician Controlled, Clinical Evaluation Of Botanical Weight Loss Formula Citrin(r). Nutracon 1995: Nutraceuticals, Dietary Supplements And Functional Foods. Day One (Sponsored by Global Business Research LTD). Published in the symposium book.
11. Thom E. (–)Hydroxycitrate (HCA) In The Treatment Of Obesity. *Int J Obesity.* 20 (4): 75 [Abstract/Poster 08-193-WP1 at 7th European Congress on Obesity in Barcelona, Spain 14–17 May, 1996].
12. Heymsfield S B, Allison D B, Vasselli J R, Pietrobelli A, Greenfield D, Nunez C. *Garcinia cambogia* (hydroxycitric acid) as a potential antiobesity agent: a randomized controlled trial. *JAMA.* 1998;280:1596–1600.
13. Majeed M., Badmaev V., Rajendran R. Potassium Hydroxycitrate For The Suppression Of Appetite And Induction Of Weight Loss. U.S. Pat. No. 5,783,603. Jul. 21, 1998.
14. Puttaparthi K, Rogers T, Elshourbagy N A, Levi M, Melnick J Z. Renal ATP citrate lyase (ATP CL) protein localizes throughout the nephron and increases only in the proximal tubule with chronic metabolic acidosis (CMA). Abstract presented at Pediatric Academic Societies' 1999 Annual Meeting. May 2, 1999; San Francisco, Calif.
15. Tanaka, T. et al. Prevention of colonic aberrant crypt foci by dietary feeding of garcinol in male F3444 rats. Carcinogenesis June 2000:21(6):1183–9.
16. Iinuma M et al. Antibacterial activity of some *Garcinia* benzophenone derivatives against methicillin-resistant Staphylococcus aureus. Biol Pharm Bull 1996 February; 19(2):311–4.
17. Krishnamurthy, N. et al. Tetrahedron Lett. 1981; 793.
18. Rao Rama, A V. et al. Chem Ind. 1979; 92.
19. Krishnamurthy, N. et al. J Food Sci and Tech. 1982;97: 19.

What is claimed:

1. A method for increasing fat catabolism in a subject in need of such effect comprising administering to said subject a fat catabolizing effective amount wherein the active ingredients in said fat catabolizing amount consists essentially of hydroxycitric acid and garcinol of hydroxycitric acid and garcinol.

2. The method of claim 1, wherein the fat catabolizing effective amount of hydroxycitric acid and garcinol further comprises anthocyanin.

3. The method of claim 1, wherein the hydroxycitric acid is extracted from fruits of *Garcinia* sp. with organic solvents.

4. The method of claim 1, wherein the garcinol is extracted from fruits of *Garcinia* sp. with organic solvents.

5. The method of claim 2, wherein the hydroxycitric acid (HCA), garcinol and anthocyanin are extracted from fruits of *Garcinia* sp. with organic solvents.

6. The method of claim 1, wherein the hydroxycitric acid is extracted from fruits of *Garcinia* sp. by $CO_2$ supereritical extraction.

7. The method of claim 1, wherein the garcinol is extracted from fruits of *Garcinia* sp. by $CO_2$ supercritical extraction.

8. The method of claim 2, wherein the hydroxycitric acid, garcinol and anthocyanin are extracted from fruits of *Garcinia* sp. by $CO_2$ supercritical extraction.

9. The method of claim 1, wherein the fat catabolizing effective amount of hydroxycitric acid and garcinol also increases lean body mass.

10. The method of claim 2, wherein the fat catabolizing effective amount of hydroxycitric acid, garcinol and anthocyanin also increases lean body mass.

11. The method of claim 1, wherein the fat catabolizing effective amount of hydroxycitric acid and garcinol also promotes weight loss.

12. The method of claim 2, wherein the fat catabolizing effective amount of hydroxycitric acid, garcinol and anthocyanin also promotes weight loss.

13. The method of claim 1, wherein the fat catabolizing effective amount of hydroxycitric acid is 500 mg.

14. The method of claim 1, wherein the fat catabolizing effective amount of garcinol is 25 mg.

15. The method of claim 2, wherein the fat catabolizing effective amounts of hydroxycitric acid, garcinol and anthocyanin are 500 mg, 25 mg, and 10 mg respectively.

16. The method of claim 1, wherein the percentage of garcinol in the fat catabolizing effective amount of hydroxycitric acid and garcinol ranges from 0.01% to 10% relative to hydroxycitric acid.

17. The method of claim 2, wherein the percentage of garcinol in the fat catabolizing effective amount of hydroxycitric acid, garcinol and anthocyanin ranges from 0.01% to 10% relative to hydroxycitric acid.

* * * * *

UNITED STATES PATENT AND TRADEMARK OFFICE
CERTIFICATE OF CORRECTION

| | |
|---|---|
| PATENT NO. | : 7,063,861 B2 |
| APPLICATION NO. | : 09/926746 |
| DATED | : June 20, 2006 |
| INVENTOR(S) | : Muhammed Majeed et al. |

It is certified that error appears in the above-identified patent and that said Letters Patent is hereby corrected as shown below:

Title Page -

Item [75], Inventors, please correct the second inventor's name from

"Vladimir Hadmaev" to -- Vladimir Badmaev --.

Signed and Sealed this

Fifteenth Day of August, 2006

JON W. DUDAS
*Director of the United States Patent and Trademark Office*